United States Patent [19]

Lee

[11] Patent Number: 5,536,703
[45] Date of Patent: Jul. 16, 1996

[54] HERBICIDAL SUBSTITUTED BENZOYL BICYCLOALKANEDIONES

[75] Inventor: Shy-Fuh Lee, Sunnyvale, Calif.

[73] Assignee: Sandoz Ltd., Basel, Switzerland

[21] Appl. No.: 372,260

[22] Filed: Jan. 13, 1995

[51] Int. Cl.⁶ .................................................. A01N 31/08
[52] U.S. Cl. .................. 504/349; 504/310; 504/315; 568/29; 568/31; 568/43; 568/37
[58] Field of Search ........................ 568/29, 31, 37, 568/43; 504/348, 349, 310, 315

[56] References Cited

U.S. PATENT DOCUMENTS

| | | | |
|---|---|---|---|
| 4,209,532 | 6/1980 | Wheeler | 504/348 |
| 4,762,551 | 8/1988 | Knudsen | 71/103 |
| 4,837,352 | 6/1982 | Knudsen | 558/396 |
| 4,854,966 | 8/1989 | Knudsen | 504/348 |
| 4,869,748 | 9/1989 | Knudsen | 71/123 |
| 4,918,236 | 4/1990 | Knudsen et al. | 568/306 |
| 4,957,540 | 9/1990 | Knudsen et al. | 71/123 |
| 4,995,902 | 2/1991 | Brunner | 71/94 |
| 5,006,158 | 4/1991 | Carter et al. | 71/98 |
| 5,089,046 | 2/1992 | Lee et al. | 71/103 |
| 5,152,826 | 10/1992 | Knudsen | 504/348 |
| 5,318,947 | 6/1994 | Ort et al. | 504/348 |
| 5,416,061 | 5/1995 | Hewett et al. | 504/348 |

FOREIGN PATENT DOCUMENTS

| | | | |
|---|---|---|---|
| 338992 | 10/1989 | European Pat. Off. | C07C 79/36 |
| 5408 | 1/1991 | Japan | A01N 41/10 |
| 120202 | 5/1991 | Japan | A01N 43/16 |
| 120203 | 5/1991 | Japan | A01N 43/90 |
| 6025144 | 1/1994 | Japan | A01N 41/12 |

*Primary Examiner*—James H. Reamer
*Attorney, Agent, or Firm*—Allen E. Norris; Lynn Marcus-Wyner

[57] ABSTRACT

The invention relates to novel thioether derivatives of substituted benzoyl bicycloalkane diones, their use as herbicides and agricultural compositions comprising the same.

9 Claims, No Drawings

HERBICIDAL SUBSTITUTED BENZOYL BICYCLOALKANEDIONES

BACKGROUND OF THE INVENTION

This invention relates to thioether derivatives of substituted benzoyl bicycloalkanediones, their use as herbicides and agricultural compositions comprising them.

Various herbicidal bicycloalkanediones are known for example from EP 338,992 and JP Kokai H6-25144.

DESCRIPTION OF THE INVENTION

It has now been discovered that certain thioether derivatives of benzoyl bicycloalkanediones which are tri-substituted in the benzene ring thereof exhibit herbicidal and plant growth regulating activity, when applied either pre or post emergence and used against annual and perennial grasses and broad leaf weeds.

The terms "herbicide" and "herbicidal" are used herein to denote the inhibitive control of modification of undesired plant growth. Inhibitive control and modification include all deviations from natural development such as, for example, total killing, growth retardation, defoliation, desiccation, regulation, stunting, tillering, stimulation, leaf burn, and dwarfing. The term "herbicidally effective amount" is used to denote any amount which achieves such control or modification when applied to the undesired plants themselves or to the area in which these plants are growing. The term "plants" is intended to include germinant seeds, emerging seedlings and established vegetation, including both roots and above-ground portions.

More particularly this invention concerns compounds of formula I

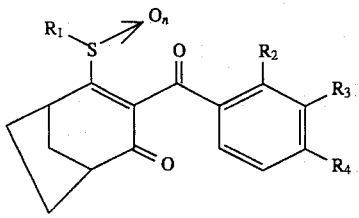

wherein
$R_1$ is lower alkyl which may be substituted with lower alkoxycarbonyl, optionally substituted aryl, optionally substituted aralkyl or cycloaklyl;
$R_2$ is halogen, lower alkyl, lower haloalkyl, or nitro;
$R_3$ is lower alkoxy, lower alkoxycarbonyl, lower alkoxyalkoxy or lower alkoxyalkyl;
$R_4$ is halogen, lower haloalkyl, lower alkylsulfonyl or lower alkylsulfonyloxy;
n is 0, 1 or 2, Lower alkyl moieties may be straight or branch chained and contain 1 to 4 carbon atoms. Cycloalkyl moieties contain 3 to 6 carbon atoms. Halogen is conveniently selected from fluorine, chlorine, bromine and iodine.

The preferred aryl moiety is phenyl. Substituents, if present on an aryl moiety are preferably selected from halogen, lower alkyl, lower alkoxy, lower haloalkyl, nitro, cyano, amino optionally mono- or di- substituted by lower alkyl, and lower alkylsulfonyl. Alkoxycarbonyl preferably contains 2 or 3 carbon atoms.

Preferred substituent meanings are as follows.
$R_1$=a) lower alkyl,
  b) aryl,
  c) ethyl,
  d) phenyl;
$R_2$=a) alkyl,
  b) halogen,
  c) methyl,
  d) chloro;
$R_3$=a) lower alkoxy,
  b) methoxy or ethoxy;
$R_4$=a) lower alkylsulfonyl
  b) methylsulfonyl;
n=0.

Combinations of these preferred meanings are especially preferred.

Two of the particularly preferred compounds are those wherein $R_1$ is ethyl or phenyl, $R_2$ is chloro, $R_3$ is methoxy, $R_4$ is methylsulfonyl and n is 0.

In general the compounds of formula I may be prepared by reacting a compound of formula II

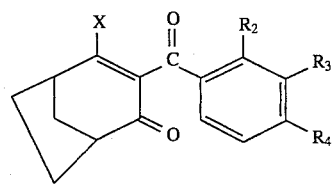

wherein X represents halogen and $R_2$, $R_3$ and $R_4$ are as defined above with a compound of formula III

$$R_1SH \qquad III$$

wherein $R_1$ is as defined above, and if a compound of formula I is desired in which n is other than 0 selectively oxidizing the compound of formula I thus obtained wherein n is 0.

The reaction of II with III may be carried out in a suitable inert solvent such as tetrahydrofuran, chloroform, dichloromethane, toluene and the like with addition of a base such as triethylamine.

Reaction temperatures conveniently lie between 0° C. and boiling point of the solvent, preferably room temperature (RT).

Oxidation of the reaction product if desired is carried out in conventional manner using an oxidizing agent such as m-chloroperbenzoic acid in an inert solvent such as dichloromethane, chloroform or carbontetrachloride.

The starting material of formula II may be prepared by halogenation of the corresponding trione of formula IV

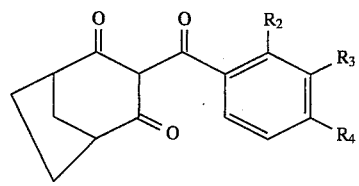

wherein $R_2$, $R_3$ and $R_4$ are as defined above.

Generally this reaction may be carried out in an inert solvent such as chloroform, carbontetrachloride, dichloromethane, dichloroethane, tetrohydrofuran, dioxane, benzene, toluene, xylene and the like. Suitable halogenation agents include a thionyl halide or an oxalyl halide in each case preferably the chloride. A catalytic amount of an amine or amide such as dimethylformamide or pyridine is also added. Reaction temperatures suitably range between RT and boiling point of the solvent.

Isolation and purification of the desired end product takes place in conventional manner. The starting materials of formula IV are either known or may be prepared in conventional manner (cf EP 338,992).

The process for making the compounds of formula I will be more fully understood by reference to the following examples.

EXAMPLE 1

Preparation of 3-(2-chloro-3-methoxy-4-methylsulfonyl-benzoyl)-4-ethyl-thio-bicyclo[3,2,1]-3-octen-2-one (Compound No.1 )

a) To a solution of 1.1 g of 3-(2-chloro-3-methoxy-4-methylsulfonyl-benzoyl)bicyclo[3,2,1]octane-2,4-dione in 20 ml of dichloromethane is added dropwise 0.5 ml oxalyl chloride at RT followed by 4 drops of dimethylformamide (DMF). The resulting mixture is refluxed for 1 hr, cooled and poured into ice-cooled $NaHCO_3$. This solution is extracted with dichloromethane and the combined extracts washed with brine, dried and evaporated to give 3-(2-chloro-3-methoxy-4-methylsulfonyl-benzoyl)-4-chloro-bicyclo[3,2,1]-3-octen-2-one as a foam.

b) To a solution of 600 mg of 3-(2-chloro-3-methoxy-4-methylsulfonyl-benzoyl)-4-chloro-bicyclo[3,2,1]-3-octen-2-one and 0.2 ml of triethylamine in 15 ml of tetrahydrofuran is added 0.2 ml of ethanethiol at RT. The resulting mixture is stirred at RT for 30 min and diluted with ethylacetate. The mixture is washed with brine and evaporated to dryness to give the title product which is purified by PTLC m.p. 127.5° C.

EXAMPLE 2

Preparation of 3-(2-chloro-3-methoxy-4-methylsulfonyl-benzoyl)-4-phenyl-thio-bicyclo[3,2,1]-3-octen-2-one (Compound No. 2)

To a solution of 650 mg of 3-(2-chloro-3-methoxy-4-methylsulfonyl-benzoyl)-4-chloro-bicyclo[ 3,2,1]-3-octen-2-one and 0.23 mg of triethylamine in 15 ml of tetrahydrofuran is added under nitrogen, 0.17 ml of thiophenol. The reaction is then continued analogously to Example 1 to yield purified title product as an oil.

NMR ($CDCl_3$) $\delta$1.55–2.09 (m, 6H, methylene H's), 2.88 (m, 1H, bridgehead H), 3.10 (m, 1H, bridgehead H), 3.25 (s, 3H, $CH_3SO_2$), 4.06 (s, 3H, $OCH_3$), 7.23 (d, 1H, benzoyl H), 7.53 (m, 5H, phenyl H's), and 7.92 (d, 1H, benzoyl H).

The compounds 3-(2-methyl-3-methoxy-4-methylsulfonyl-benzoyl)-4-ethylthiobicyclo[3,2,1 ]-3-octen-2-one (Compound No. 3) and 3-(2-methyl-3-methoxy-4-methylsulfonyl-benzoyl)- 4-phenylthio-bicyclo[3,2,1]-3-octen-2-one (Compound No. 4) may be prepared analogously.

EXAMPLE 3

The test compounds are weighed and dissolved in a stock solution consisting of acetone:deionized water (1:1) and 0.5% adjuvant mixture. Dilutions from this stock solution are performed to allow for preparation of spray solutions consisting of single doses applied at a level equivalent to either 4.0, 1.0 or 0.25 kg/ha of active ingredient. The solutions are applied by a linear track sprayer set to deliver 1000 L/ha spray volume.

In pre-emergent studies, each dose of herbicide is applied as a band treatment over the seed zone. Pots containing the seeds are then top-dressed with soil, the plants are grown in the greenhouse and visually evaluated 7 and 19 days after treatment.

In post-emergence studies, each dose of compound is applied to the foliage of the selected weed seedling species. The plants are allowed to grow in the greenhouse and visually evaluated at 1, 7 and 19 days after treatment. Weed species tested are shown in Table 1. Herbicidal control is evaluated as % injury with 100% injury considered complete control. At an application rate of 1.0 kg/ha active ingredient the compound nos 1 and 2, exhibited herbicidal control at 80% or greater for various tested weeds in both pre-emergence and post-emergence screenings. It is understood that this example does not reflect all obtained data.

TABLE 1

| Common Name | Genus Species |
| --- | --- |
| Velvetleaf | *Abutilon theophrasti* |
| Redroot Pigweed | *Amaranthus retroflexus* |
| Mustard White | *Sinapis alba* |
| Black Nightshade | *Solanum nigrum* |
| Wild Oat | *Avena fatua* |
| Downy Brome | *Bromus tectorum* |
| Barnyardgrass | *Echinochloa crus-galli* |
| Green Foxtail | *Setaria viridis* |

METHODS OF APPLICATION

Application of a compound of formula I is made according to conventional procedure to the weeds or their locus using a herbicidally effective amount of the compound, usually from 1 g to 10 kg/ha.

Compounds according to the invention may be used for the control of both broadleaf and grassy weeds in both preplant incorporation and pre- and post-emergent application. Compounds may also exhibit selectivity in various crops and may thus be suited for use in weed control in crops such as but not limited to corn, cotton, wheat, soybean and rice.

The optimum usage of a compound of formula I is readily determined by one of ordinary skill in the art using routine testing such as greenhouse testing and small plot field testing. It will depend on the compound employed, the desired effect (a phytotoxic effect requiring a higher rate than a plant growth regulating effect), the conditions of treatment and the like. In general, satisfactory phytotoxic effects are obtained when the compound of formula I is applied at a rate in the range of from 0.001 to 5.0 kg, more preferably of from 0.005 to 2.5 kg per hectare, especially 0.01 to 1.0 kg per hectare.

The compounds of formula I may be advantageously combined with other herbicides for broad spectrum weed control. Examples of herbicides which can be combined with a compound of the present invention include those selected from carbamates, thiocarbamates, chloroacetamides, triazines, dinitroanilines, benzoic acids, glycerol ethers, pyridazinones, uracils, phenoxys and ureas for controling a broad spectrum of weeds.

The compounds of formula I are conveniently employed as herbicidal compositions in association with agriculturally acceptable diluents. Such compositions also form part of the present invention. They may contain, aside from a compound of formula I as active agent, other active agents, such as herbicides or compounds having antidotal, fungicidal, insecticidal or insect attractant activity. They may be employed in either solid or liquid forms such as a wettable powder, an emulsifiable concentrate, a granule or a microcapsule incorporating conventional diluents. Such compositions may be produced in conventional manner, for example by mixing the active ingredient with a diluent and optionally other formulating ingredients such as surfactants.

Agriculturally acceptable additives may be employed in herbicidal compositions to improve the performance of the active ingredient and to reduce foaming, caking and corrosion, for example.

The term "diluent" as used herein means any liquid or solid agriculturally acceptable material which may be added to the active constituent to bring it in an easier or improved applicable form, respectively, to a usable or desirable strength of activity. It can for example be talc, kaolin, diatomaceous earth, xylene or water.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

Particularly formulations to be applied in spraying forms such as water dispersible concentrates or wettable powders may contain surfactants such as wetting and dispersing agents, for example the condensation product of formaldehyde with naphthylene sulphonate, an ethoxylated alkylphenol and an ethoxylated fatty alcohol.

In general, the formulations include from 0.01 to 99% by weight of active agent and from 0 to 20% by weight of agriculturally acceptable surfactant, and from 0.1 to 99.99% of solid or liquid diluent(s) the active agent consisting either of at least one compound of formula I or mixtures thereof with other active agents. Concentrate forms of compositions generally contain between about 2 and 95%, preferably between about 10 and 90% by weight of active agent.

Typical herbicidal compositions, according to this invention, are illustrated by the following Examples A, B, C and D in which the quantities are in pans by weight.

EXAMPLE A

Preparation of a Wettable Powder

25 Parts of a compound according to this invention are mixed and milled with 25 parts of synthetic fine silica, 2 parts of sodium lauryl sulphate, 3 pans of sodium lignosulfonate and 45 pans of finely divided kaolin until the mean particle size is about 5 micron. The resulting wettable powder is diluted with water to a desired concentration.

EXAMPLE B

Preparation of Water Dispersible Granule

40 Parts of a water insoluble compound according to this invention are wet milled in a solution of 10 parts MARASP-ERSE N-22 (a sodium lignosulfonate) and 50 parts water until a median particle size of 5 micron is reached. The slurry is spray dried on a NIRRO MOBILE MINOR unit at an inlet temperature of 150° C. and outlet temperature of 70° C. The resulting granule can be readily dispersed in water for application.

EXAMPLE C

Preparation of a Microcapsule Suspension (a) 0.38 Pans of a VINOL 205 (a partially hydrolyzed polyvinyl alcohol) are dissolved in 79.34 pans water.

(b) 3.75 Parts of an organic soluble compound according to this invention are dissolved in 3.75 pans TENNECO 500–100 (a xylene range aromatic solvent). To this solution are added 0.63 pans of SEBACOYL CHLORIDE and 0.88 parts PAPI 135 (polymethylene isocyanate).

(c) 1.89 Parts piperazine and 0.50 parts of NaOH are dissolved in 12.60 pans of water.

Transfer premix (a) to a one quart osterizer and while stirring add premix (b) and sheer for approximately 60 seconds or until a droplet size of 10–20 microns is reached. Immediately add premix (c), continue stirring for 3 hours and neutralize with acetic acid. The resulting capsule suspension may be diluted in water for spraying.

EXAMPLE D

Preparation of an Emulsifiable Concentrate

13 Parts of an organic soluble compound according to this invention are dissolved in 79 parts of TENNECO 500-100 along with 2 parts TOXIMUL RHF and 6 parts TOXIMUL S. TOXIMULS are a "matched pair"; each containing anionic and nonionic emulsifiers. The stable solution will spontaneously emulsify in water for spraying.

What is claimed is:

1. Compounds of formula I

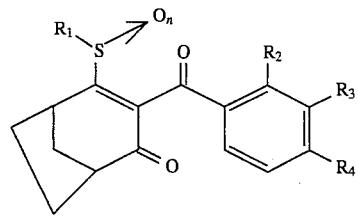

wherein
$R_1$ is lower alkyl which may be substituted with lower alkoxycarbonyl or cycloalkyl; or phenyl or phenalkyl which may be substituted by one or more substituents selected from halogen, lower alkyl, lower alkoxy, lower haloalkyl, nitro, cyano, amino optionally mono- or di-substituted by lower alkyl and lower alkylsulfonyl $R_2$ is halogen, lower alkyl, lower haloalkyl, or nitro;

$R_3$ is lower alkoxy, lower alkoxycarbonyl, lower alkoxyalkoxy or lower alkoxyalkyl;

$R_4$ is halogen, lower haloalkyl, lower alkylsulfonyl or lower alkylsulfonyloxy;

n is 0, 1 or 2.

2. A compound according to claim 1 wherein $R_1$, $R_2$, $R_3$ and $R_4$ are independently selected from the following meanings R=a) lower alkyl,
  b) aryl,
  c) ethyl,
  d) phenyl;

$R_2$=a) lower alkyl,
  b) halogen,
  c) methyl,
  d) chloro;

$R_3$=a) lower alkoxy,
  b) methoxy or ethoxy;

$R_4$ =a) lower alkylsulfonyl
  b) methylsulfonyl.

3. A compound according to claim 1 wherein n is 0.

4. A compound according to claim 2 wherein $R_1$ is ethyl or phenyl, $R_2$ is methyl or chloro, $R_3$ is methoxy, $R_4$ is methylsulfonyl and n is 0.

5. A compound according to claim 4 wherein $R_2$ is chloro.

6. A herbicidal composition comprising an herbicidally effective amount of a compound of claim 1 in association with an agriculturally acceptable diluent.

7. A method for controlling undesirable weed pests which comprises applying to the locus where control is desired an herbicidally effective amount of a compound of claim 1.

8. A method for controlling undesirable pests according to claim 7 wherein the compound is applied pre-emergent.

9. A method for controlling undesirable pests according to claim 7 wherein the compound is applied post-emergent.

* * * * *